United States Patent [19]

Stoub

[11] Patent Number: 5,650,625
[45] Date of Patent: Jul. 22, 1997

[54] TWO-DIMENSIONAL RADIATION EMITTER FOR ATTENUATION CORRECTION IN NUCLEAR MEDICINE STUDIES

[75] Inventor: Everett W. Stoub, Crystal Lake, Ill.

[73] Assignee: Siemens Medical Systems, Inc., Iselin, N.J.

[21] Appl. No.: 559,748

[22] Filed: Nov. 15, 1995

Related U.S. Application Data

[63] Continuation-in-part of Ser. No. 491,422, Jun. 16, 1995.
[51] Int. Cl.$^6$ .................................................. G21K 5/00
[52] U.S. Cl. ................................. 250/363.04; 250/494.1
[58] Field of Search .......................... 250/494.1, 496.1, 250/363.04

[56] References Cited

U.S. PATENT DOCUMENTS 5,055,687  10/1991  Ichihara ..................... 250/363.04 X
5,210,421   5/1993  Gullberg et al. ............... 250/363.04
5,479,021  12/1995  Morgan et al. ................. 250/363.04

OTHER PUBLICATIONS

Jaszczak et al., "Fast Transmission CT for Determining Attenuation Maps Using a Collimated Line Source, Rotatable Air–Copper–Lead Attenuators and Fan–Beam Collimation", The Journal of Nuclear Medicine, vol. 34, No. 9, Sep. 1993, pp. 1577–1586.

*Primary Examiner*—Edward J. Glick
*Attorney, Agent, or Firm*—Mark H. Jay

[57] ABSTRACT

A two-dimensional radiation emitter has a plurality of line sources, advantageously of Gd-153. The line sources are removeably retained in the emitter, and form an array. The most active line sources are located in the center region of the array, and the activity of the sources progressively diminishes from the center of the array to the ends of the array (where the least active line sources are located). As the line sources undergo radioactive decay, they are moved towards the ends.

7 Claims, 6 Drawing Sheets

TWO-DIMENSIONAL RADIATION EMITTER FOR ATTENUATION CORRECTION IN NUCLEAR MEDICINE STUDIES

BACKGROUND OF THE INVENTION

This application is a continuation in part of commonly owned application Ser. No. 08/491,422, filed Jun. 16, 1995. The contents of this parent patent application, including the drawings therein, are hereby incorporated into this continuation in part application, as if fully disclosed herein.

The referenced application discloses a scanning line source that is reoriented to be parallel with the axis of rotation of the scintillation camera system. The referenced application also discloses a scanning line source that produces a minimum radiation density at extreme off-axis positions and a maximum radiation density adjacent the axis of rotation. This gradient radiation density has two advantages. First, it prevents the source from producing "hot spots" at detector regions that are directly exposed to the line source. Second, it also permits maximum radiation density to be output at the center of the patient's body, thereby increasing the quantity of transmission CT data collected there and making it possible to more precisely determine the attenuation caused by the patient's body.

The scanning line source disclosed in the referenced patent application has certain disadvantages. While it is mechanically simple, it does have a mechanism and mechanisms can malfunction. Additionally, the disclosed scanning line source would use Gd-153 (the preferred radioisotope) in an economically inefficient manner.

This economic inefficiency comes about because the disclosed line source must produce a high radiation density adjacent the axis of rotation. After some time, radioactive decay will reduce the activity of the line source, and the line source will then need replacement. When such replacement is carried out, the line source will still have significant activity (i.e. will still contain a substantial quantity of Gd-153). As a result, each time the line source is replaced, a significant quantity of residual Gd-153 will be wasted. Furthermore, because Gd-153 has an 8 month half-life, and because it would not be practical to keep the line source more than about 4 months (during which time the activity of the line source would decrease by about 30%), this waste of residual Gd-153 will occur three times each year, at substantial cost.

It therefore is one object of the invention to provide a radiation emitter for use with a scintillation camera system, which radiation emitter has no moving parts.

Another object is to provide such an emitter that can be used in such as manner as to reduce the radioactive waste produced during normal use, thereby preventing the economic waste associated with disposal of such waste.

Another object is, in general, to improve on known radiation emitters of this general type.

In accordance with the invention, there is provided a two-dimensional radiation emitter for use with a scintillation camera system to carry out attenuation correction. The emitter has an array formed of a plurality of parallel, elongated line sources of equal length. A support supports the line sources parallel to the axis of rotation of the camera system.

Advantageously, and in accordance with one preferred embodiment, the emitter is shaped as an elongated rectangle having two long sides and two ends. The ends are approximately as long as the line sources, and the line sources are located between the ends of the emitter to form a pattern that is symmetrical with respect to the center of the emitter. Further advantageously, and likewise in accordance with the preferred embodiment, the line sources have different activities, i.e. produce different radiation densities. More particularly, the line sources in the central region of the array have maximum activities and the line sources at the ends of the array have minimum activities. The emitter is thereby provided with a gradient radiation density, i.e. it produces a radiation density that varies with location; in the preferred embodiment, this radiation density is maximum at the center, minimum at the ends, and decreases monotonically from the center to the ends.

In another preferred embodiment, the line sources with maximum activities are not centered with respect to the emitter. This alternate preferred embodiment is useful for 90° cardiac studies.

In a particularly advantageous construction, and as in the first preferred embodiment, the line sources can be moved between different predetermined locations in the support and there are an even number of line sources defining a plurality of line source pairs. Each of the line sources in a single pair have approximately the same activity, and the activities of the sources decrease in equal predetermined fractional steps from the center of the array to the ends of the array.

By using this construction, new line sources may installed in central locations of the emitter (where a high radiation density is required because of the high attenuation of the patient's body). As each line source undergoes radioactive decay, it is progressively moved outwardly from its original position. Once the source has been moved to an end location and radioactive decay renders it no longer usable, it is discarded. In this way, a line source remains in use until its deterioration by radioactive decay is almost complete. This produces only a minimum quantity of radioactive waste.

BRIEF DESCRIPTION OF THE DRAWINGS

The invention will be better understood with reference to the following illustrative and non-limiting drawings, in which.

DETAILED DESCRIPTION OF PREFERRED EMBODIMENTS

Figure 1:
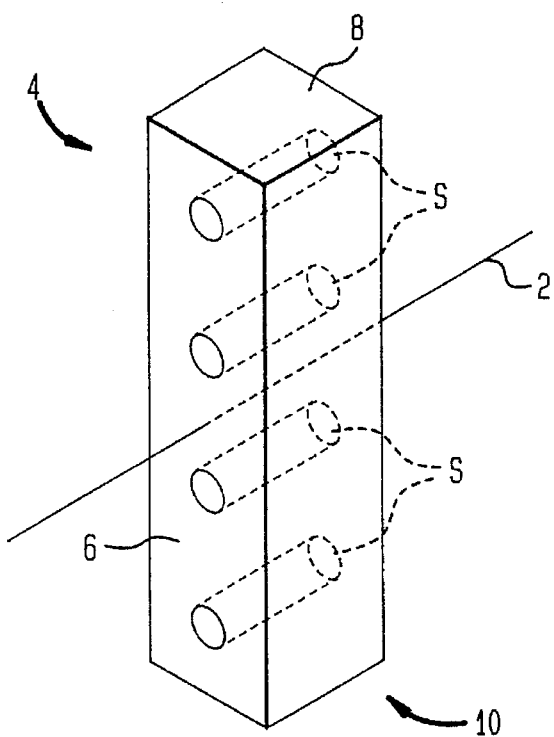
FIG. 1 is a generalized schematic drawing of the preferred embodiment of the invention.

In a scintillation camera system (not shown) for use in SPECT, the detector(s) (not shown) rotate(s) around an axis 2 and a radiation emitter generally indicated by reference numeral 4 is used to supply gamma radiation that is used to determine transmission CT data. In a preferred embodiment of the invention, the emitter 4 has an elongated frame 6 (shown in more detail in FIG. 6) with ends 8 and 10, into which frame 6 twenty Gd-153 line sources S may be removeably placed. (Although Gd-153 is the preferred isotope, another isotope may be used instead. The number of line sources S is not a part of the invention, and more or fewer line sources S may be used instead. As will be seen below, in the preferred embodiment of the invention, the line sources S may be different from each other, but all have the same external dimensions.)

When the line sources S are placed in the frame 6, the line sources S form a twenty-location array (see FIG. 2) that is centered on the axis 2. In this example, the array is a simple series of parallel lines spaced at regular intervals between the ends 8 and 10. The locations of the array are shown by reference numerals 12, 14, 16, 18, 20, 22, 24, 26, 28, 30, 32, 34, 36, 38, 40, 42, 44, 46, 48 and 50; these locations are parallel to the axis A (and may, if desired, be coplanar). In the preferred embodiment, each of the line sources S is approximately six inches long and each of the locations 12 ... 50 is spaced one inch away from its neighbors, producing an emitter 4 that is approximately six inches wide and twenty inches long. (Although regular spacing of the line sources S is presently preferred, this is not necessary; other patterns can be used instead. The array in accordance with the first preferred embodiment of the invention is symmetrical with respect to its center. Neither the six inch width nor the twenty inch length of the emitter 4 is part of the invention. In the preferred embodiment, the six inch length is chosen to facilitate cardiac studies and the twenty inch length corresponds to one of the dimensions of the rectangular detector with which the emitter 4 is used.)

Figure 2:
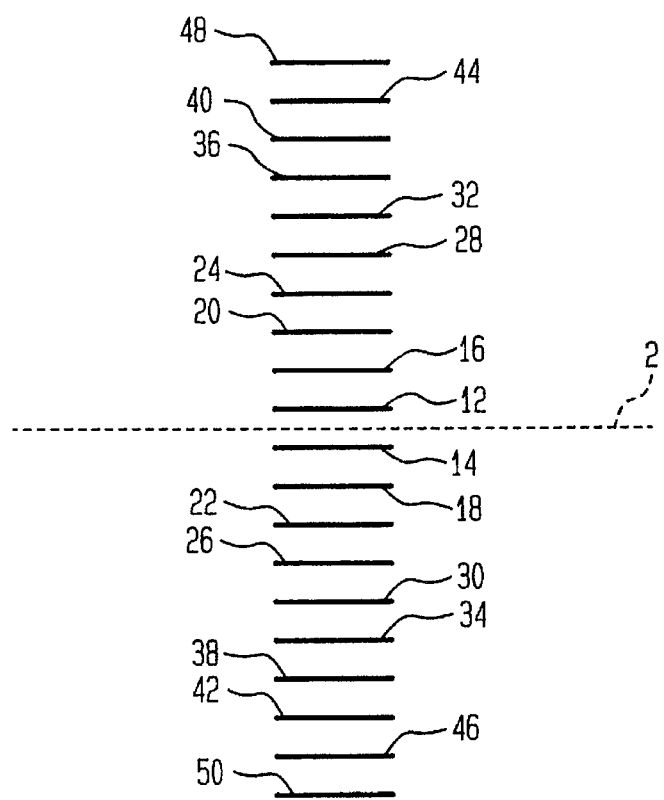
FIG. 2 shows the array of line sources used in the preferred embodiment of the invention.

As can be seen in FIG. 2, the pair of line sources S at positions 12 and 14 is at the center of the array and is centered on the axis 2. Another pair of line sources S at positions 16 and 18 is adjacent the pair of line sources S at positions 12 and 14 respectively and is likewise centered; similarly centered line source pairs extend outwardly from the center of the array to the line source pair that includes the line sources S at positions 48 and 50. As a result, there are ten pairs of line sources S, each pair including two line sources S that are equidistant from the center of the array.

In the preferred embodiment, line sources S in each pair have approximately the same activity (quantity of radioactive material, expressed in mCi, therefore producing the same radiation density) but the activity changes progressively from one pair to the next in equal fractional steps. Since Gd-153 has a half-life of eight months, four months of radioactive decay causes any particular Gd-153 line source to lose approximately 30% of its activity (i.e. approximately 30% of the Gd-153 decays to another isotope during this period of time). Advantageously, and in accordance with the preferred embodiment, with each outward step, each pair of line sources S has an activity diminished by 30% from the immediately preceding pair. This produces the activity profile shown in FIG. 3 (which is based on a maximum activity of 8.31 mCi for each of the line sources S in the central pair at locations 12 and 14.)

Figure 3:
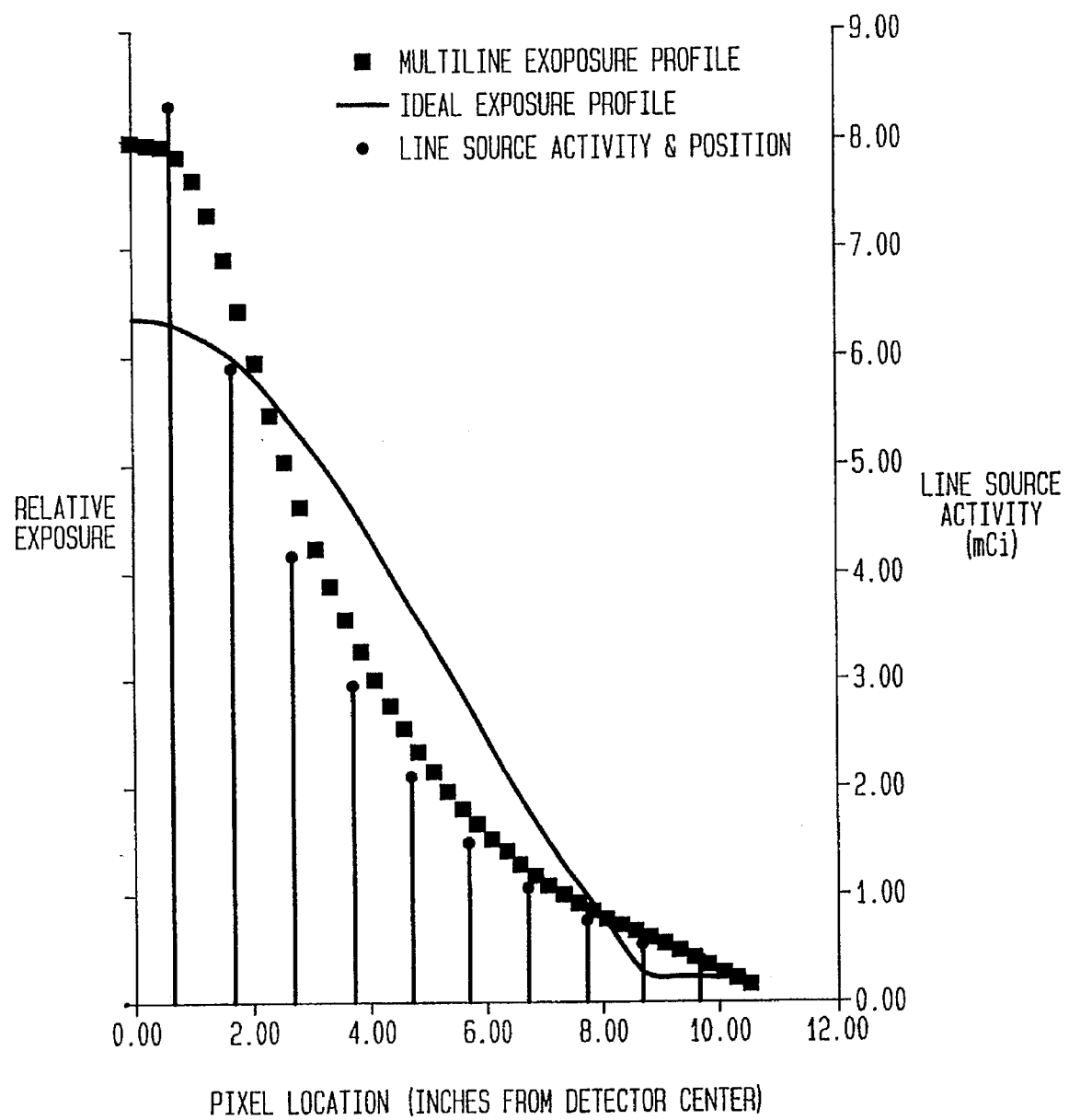
FIG. 3 illustrates the activity profile used in the first preferred embodiment of the invention.

As will now be explained, this activity profile, combined with the way in which the line sources S are retained in the frame 6, makes it possible to use the Gd-153 very efficiently. Because the line sources S have the same external dimensions and are removeably retained within the frame 6, any line source can be removed from one of the locations 12 .. . 50 and reinstalled at any other one of the locations 12 .. . 50. Let it be assumed that four months elapses from the time the activity profile is as shown in FIG. 3. At this later time, the line sources S at locations 48 and 50 will have undergone such extensive radioactive decay that they will be discarded. The line sources S at locations 44 and 46 will then be moved to locations 48 and 50, the line sources S at locations 40 and 42 will then be moved to locations 44 and 46, and so on until the line sources S at locations 12 and 14 have been moved to locations 16 and 18. Finally, new line sources S will be installed at positions 12 and 14.

With this scheme, it is only necessary to purchase approximately 16.62 mCi of Gd-153 every four months, and only a minute quantity (approximately 0.5 mCi) of Gd-153 is discarded every four months. In this manner, a gradient radiation density is produced while using line sources S in a very efficient manner.

Figure 4:
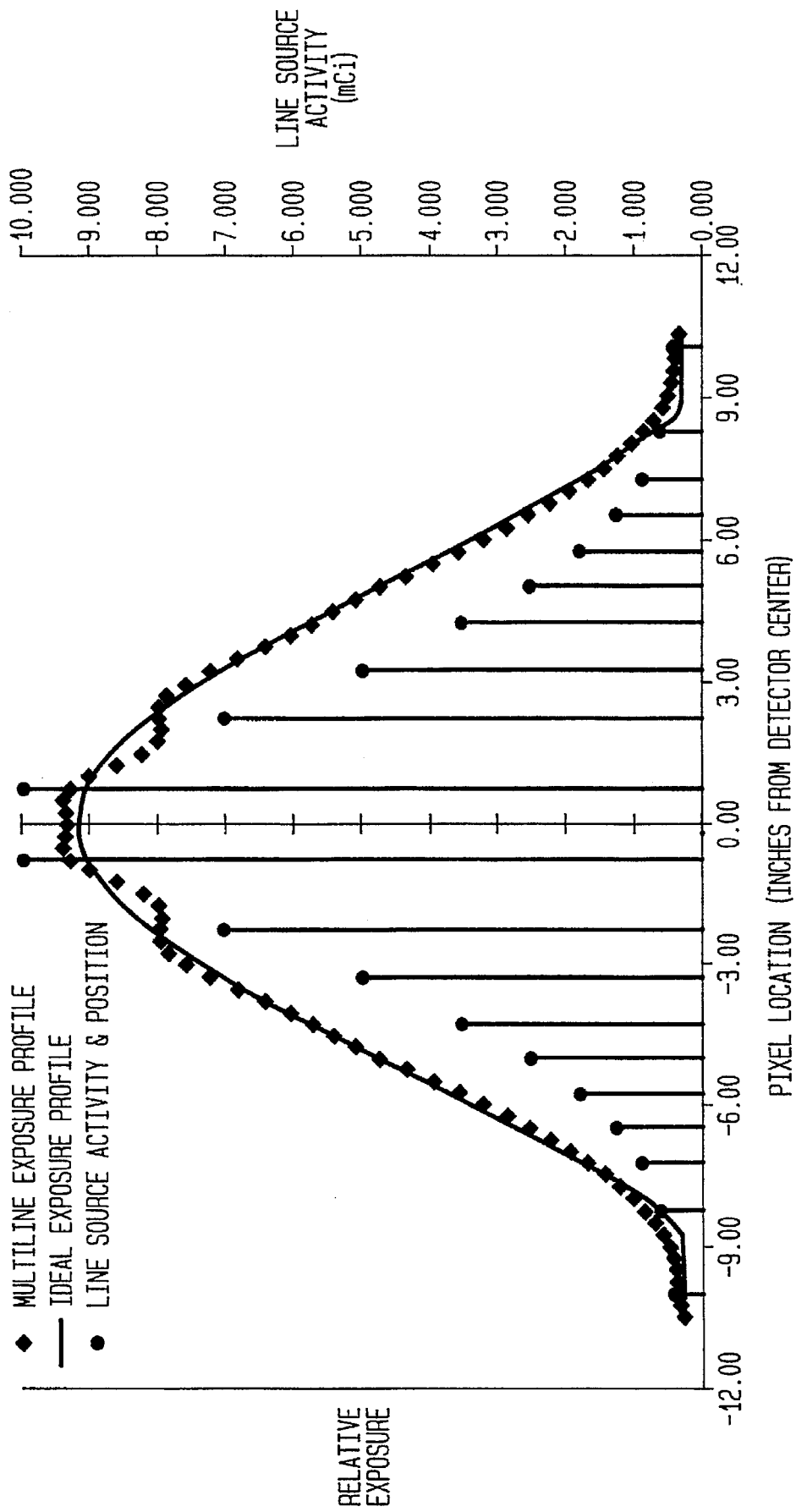
FIG. 4 illustrates an activity profile that may be used in an alternate embodiment of the invention.

The activity profile illustrated in FIG. 3 corresponds well to the ideal exposure profile for a 325 lb. patient (this is a design target). The average radiation attenuation of such a patient can be accurately modeled using a cylinder of seventeen inches diameter, attenuating at the rate of 41% per inch. As can be seen from FIG. 3, which assumes that such a patient is interposed midway between an emitter 4 and a detector (not shown) that are spaced apart by approximately one meter, this activity profile corresponds well to the ideal exposure profile. To improve the correspondence, the array pattern may be changed; an optimized pattern, and the activity profile it produces, is shown in FIG. 4.

Figure 5:
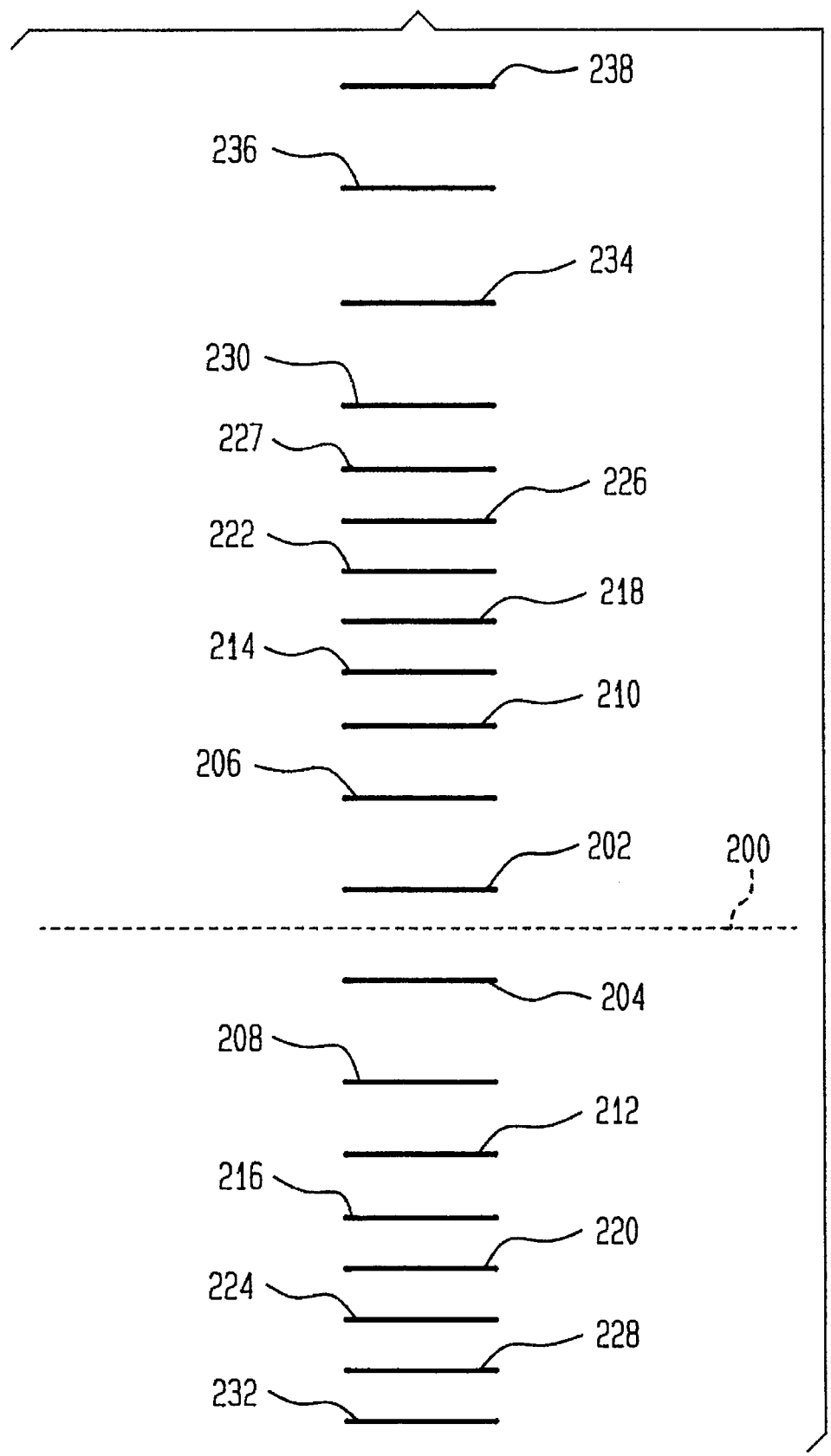
FIG. 5 shows the array of line sources used in the second preferred embodiment of the invention.
Figure 6:
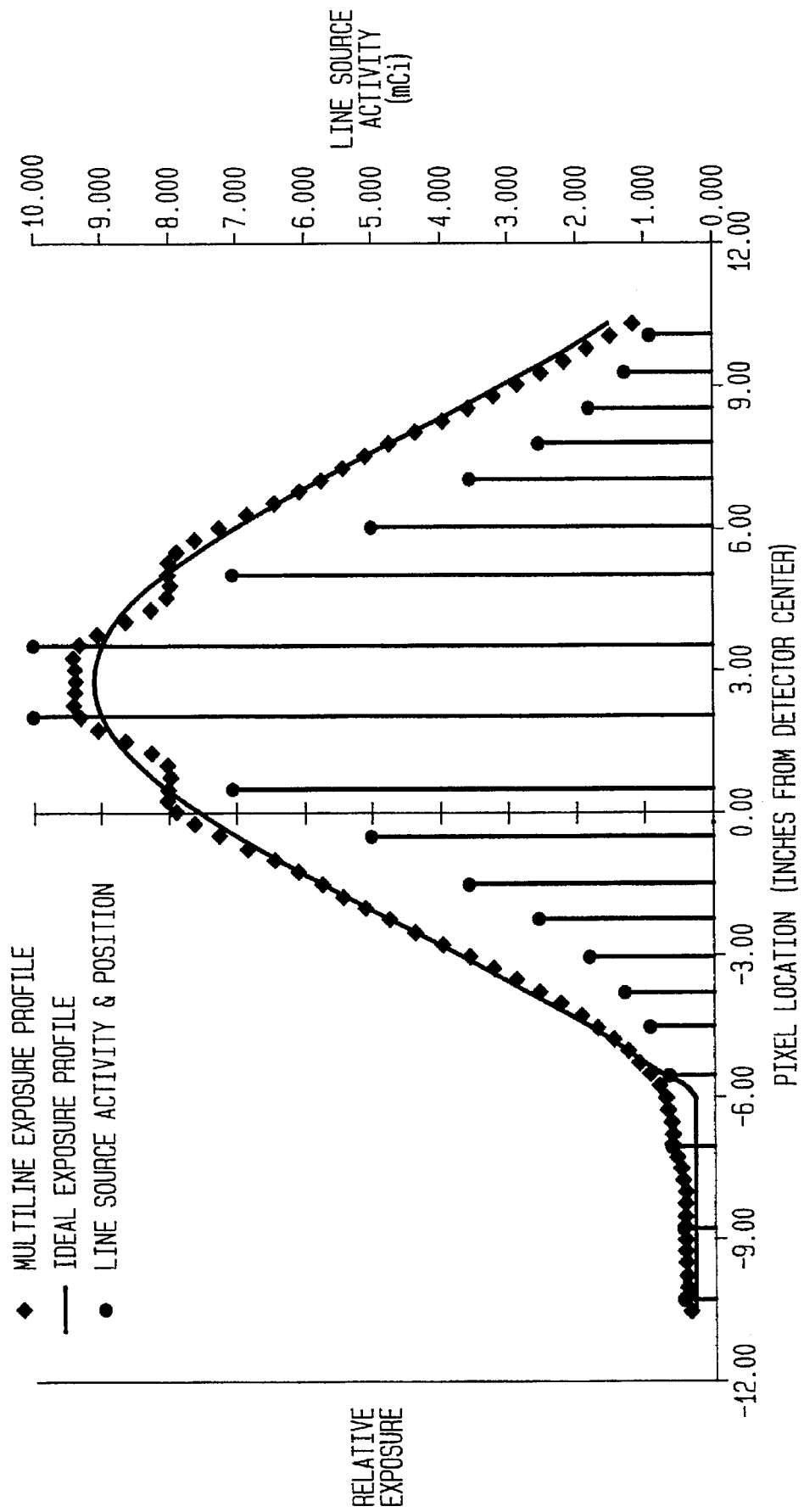
FIG. 6 illustrates the activity profile used in the second preferred embodiment of the invention.

In accordance with a second preferred embodiment of the invention as illustrated in FIGS. 5 and 6, the activity profile is asymmetric with respect to the center of the emitter. This activity profile is useful for 90° cardiac imaging studies, where the axis 200 of the patient is not aligned with the axis 2.

Because the array pattern is asymmetric in the second preferred embodiment, the line sources are moved along a more complicated path as radioactive decay progresses. Initially, new maximum-activity line sources S are placed at locations 202 and 204 (FIG. 5). After four months, the line souces S are relocated from locations 202 and 204 to locations 206 and 208 respectively. Four months later, they are respectively moved to locations 210 and 212, and at successive four month intervals, the line sources S move:

to locations 214 and 216;
then to locations 218 and 220;
then to locations 222 and 224;
then to locations 226 and 228; and
then to locations 227 and 232.

Four months later, the line source S at location 232 is moved to location 234 and the line source S at location 227 is moved to location 230. Four months afterward, the line sources S at locations 236 and 238 are discarded and the line sources S at locations 230 and 234 are moved to locations 236 and 238. With this scheme, the activity profile of the second preferred embodiment is as illustrated in FIG. 6.

Figure 7:
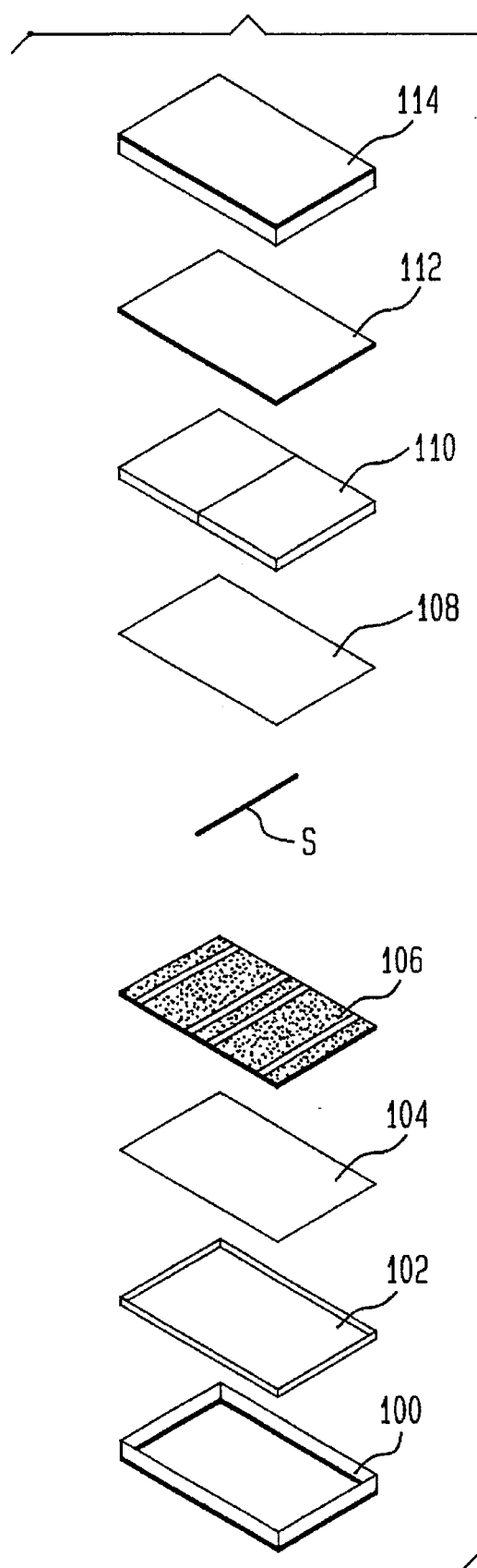
FIG. 7 schematically illustrates the mechanical structure of the first preferred embodiment of the invention.

FIG. 7 shows a presently-preferred mechanical structure in accordance with the a preferred embodiment of the invention. As illustrated, the frame 6 is made up of a series of parts. On the bottom of the frame 6, i.e. on the side of the emitter 4 that faces away from the scintillation camera detector (not shown) is a bottom cover 100 made of e.g. aluminum. Inside the bottom cover 100 is a sheet 102 of lead. The lead sheet 102 is a shield that blocks gamma radiation from exiting the bottom of the frame 6. On top of the lead sheet 102 is located a sheet 104 of tin. The purpose of the sheet 104 is to filter the radiation from the Gd-153 line sources, thereby preventing the lead in the sheet 102 from fluorescing (and thereby producing 70–80 keV radiation) as a result of irradiation by Gd-153 gamma radiation. On top of the tin sheet 104 is a plexiglass sheet 106. The top surface of the plexiglass sheet 106 has twenty grooves. The grooves have identical dimensions, suitable for properly positioning the Gd-153 line sources S (for clarity, only one line source S is shown). When the Gd-153 line sources are to be moved from one location to another, they are simply rolled or otherwise moved into a different groove. On top of the Gd-153 line sources is located a sheet 108 of copper. The copper sheet 108 blocks 44 keV radiation from the Gd-153 line sources that would otherwise be detected by the detector. Finally, on top of the copper sheet 108 is located a collimator 110.

The collimator 110 is provided so that radiation from the emitter 4 is emitted in directions that roughly match the design characteristics of the collimated detector opposed to it. Such matching maximizes the chance that gamma radiation emitted by the emitter 4 will actually be detected by the detector and not blocked by the detector collimator. In the preferred embodiment, the collimator 110 is made of a lead core configured as an Ultra-High-Sensitivity collimator having an acceptance angle of 12.4°. This collimator 110 is chosen for applications where the detector (not shown) is collimated with a High Resolution collimator having an acceptance angle of 5.4°.

Advantageously, a lead stop sheet 112 is detachably securable to the collimator 110 using a cover 114. The stop sheet 112 is secured to the collimator 110 when the emitter is not in use, to prevent unnecessary irradiation of personnel. When the emitter is to be used, the cover 114 and stop sheet 112 are removed.

Persons skilled in the art will understand that the shape of the array, and the activities of the line sources in the array, can be changed to correspond to any desired gradient radiation density.

Although a preferred embodiment has been described above, the scope of the invention is limited only by the following claims:

I claim:

1. A two-dimensional radiation emitter for use with a scintillation camera system to carry out attenuation correction, said emitter being shaped as an elongated rectangle having two long sides and two ends and producing a gradient radiation density, comprising:

an array formed of a plurality of parallel, elongated line sources of equal length and different activities, said line sources being parallel to and approximately as long as said ends; and a support, the support supporting said line sources in a plane to be parallel to the axis of rotation of the camera system.

2. The emitter of claim 1, wherein the array is symmetrical about its center, wherein line sources in the center of the array have maximum activities, and wherein line sources at the ends of the array have minimum activities.

3. The emitter of claim 2, wherein there are an even number of line sources defining a plurality of line source pairs, each of the line sources in a single pair having approximately the same activity, and wherein the activities of the sources decrease in equal predetermined fractional steps from the center of the array to the ends of the array.

4. The emitter of claim 1, wherein the line sources are moveable between different predetermined locations in the array.

5. The emitter of claim 1, wherein the line sources are of Gd-153.

6. The emitter of claim 1, wherein the array is asymmetric about its center.

7. A two-dimensional radiation emitter for use with a scintillation camera system to carry out attenuation correction, said emitter producing a gradient radiation density, comprising:

an array formed of a plurality of parallel, elongated line sources of equal length and different activities; and a support, the support supporting said line sources in a plane to be parallel to the axis of rotation of the camera system.

* * * * *